US009974634B2

(12) United States Patent
Maloney et al.

(10) Patent No.: US 9,974,634 B2
(45) Date of Patent: May 22, 2018

(54) METHODS FOR WHITENING TEETH

(71) Applicant: Colgate-Palmolive Company, New York, NY (US)

(72) Inventors: Venda Porter Maloney, Piscataway, NJ (US); Dennis Ontumi, Easton, PA (US); Suman Chopra, Monroe, NJ (US); Rajnish Kohli, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

(21) Appl. No.: 14/650,734

(22) PCT Filed: Dec. 14, 2012

(86) PCT No.: PCT/US2012/069835
§ 371 (c)(1),
(2) Date: Jun. 9, 2015

(87) PCT Pub. No.: WO2014/092730
PCT Pub. Date: Jun. 19, 2014

(65) Prior Publication Data
US 2015/0305843 A1    Oct. 29, 2015

(51) Int. Cl.
```
A61C 15/00    (2006.01)
A61K 8/00     (2006.01)
A61C 19/06    (2006.01)
A61Q 11/00    (2006.01)
A61K 8/81     (2006.01)
A61K 8/22     (2006.01)
A61K 8/38     (2006.01)
A61K 8/42     (2006.01)
```

(52) U.S. Cl.
CPC ............ *A61C 19/066* (2013.01); *A61K 8/22* (2013.01); *A61K 8/38* (2013.01); *A61K 8/42* (2013.01); *A61K 8/8176* (2013.01); *A61Q 11/00* (2013.01); *A61K 2800/28* (2013.01); *A61K 2800/87* (2013.01)

(58) Field of Classification Search
USPC ........................................... 424/49; 433/216
See application file for complete search history.

(56) References Cited

U.S. PATENT DOCUMENTS

| | | | |
|---|---|---|---|
| 4,485,089 A | 11/1984 | Leipoid | |
| 4,564,514 A | 1/1986 | Drauz et al. | |
| 4,788,052 A | 11/1988 | Ng et al. | |
| 4,837,008 A | 6/1989 | Rudy et al. | |
| 4,891,211 A | 1/1990 | Winston | |
| 4,897,258 A | 1/1990 | Rudy et al. | |
| 4,971,782 A | 11/1990 | Rudy et al. | |
| 4,986,981 A | 1/1991 | Glace et al. | |
| 5,008,093 A | 4/1991 | Merianos | |
| 5,077,047 A | 12/1991 | Biss et al. | |
| 5,108,742 A | 4/1992 | Merianos | |
| 5,122,370 A | 6/1992 | Merianos et al. | |
| 5,130,124 A | 7/1992 | Merianos et al. | |
| 5,256,402 A | 10/1993 | Prencipe et al. | |
| 5,310,563 A | 5/1994 | Curtis et al. | |
| 5,312,619 A | 5/1994 | Shih et al. | |
| 5,374,368 A | 12/1994 | Hauschild | |
| 5,401,495 A | 3/1995 | Murayama | |
| 5,424,060 A | 6/1995 | Hauschild | |
| 5,425,953 A | 6/1995 | Sintov et al. | |
| 5,496,542 A | 3/1996 | Hauschild | |
| 5,614,174 A | 3/1997 | Hsu et al. | |
| 5,676,933 A | 10/1997 | Hauschild | |
| 5,718,886 A | 2/1998 | Pellico | |
| 5,776,435 A | 7/1998 | Gaffar et al. | |
| 5,885,555 A | 3/1999 | Sheehan | |
| 5,945,032 A | 8/1999 | Breitenbach et al. | |
| 6,083,421 A | 7/2000 | Huang et al. | |
| 6,221,341 B1 | 4/2001 | Montgomery | |
| 6,447,757 B1 | 9/2002 | Orlowski et al. | |
| 6,514,484 B2 | 2/2003 | Rajaiah et al. | |
| 6,514,543 B2 | 2/2003 | Montgomery | |
| 6,555,020 B1 | 4/2003 | Chadwick et al. | |

(Continued)

FOREIGN PATENT DOCUMENTS

| CA | 2484372 | 3/2006 |
|---|---|---|
| DE | 2365631 | 10/1975 |

(Continued)

OTHER PUBLICATIONS

D, 2011, "If you rub whitening toothpaste on your teeth and leave it overnight will it whiten them and is it bad?" Yahoo Canada Answers http://ca.answers.yahoo.com/question/index?qid=20110723200617AAmNciz.
International Search Report and Written Opinion in International Application No. PCT/US2006/035278, dated Feb. 12, 2007.
International Search Report and Written Opinion in International Application No. PCT/US2012/069835, dated Oct. 30, 2013.
International Specialty Products, 2003, "Applications—Toothpaste and Mouthwash", ISP Polymers for Oral Care, 10 pgs.
International Specialty Products, 2003, "Product and Applications Guide," ISP Polymers for Oral Care, 19 pgs.
Joiner et al., 2008, "A Review of Tooth Colour and Whiteness," J. Dentistry 36S(1):S2-7.
Joiner, 2004, "Tooth Colour: A Review of the Literature," J. Dentistry 32(1):3-12.

(Continued)

*Primary Examiner* — Nicole F Johnson
*Assistant Examiner* — Nicole F. Lavert

(57) ABSTRACT

Described herein are regimens for whitening the teeth, comprising administering to the teeth an effective amount of a first oral care composition comprising a bleaching agent and allowing the first oral care composition to remain on the teeth for at least 30 seconds, and brushing the teeth with a second oral care composition. Kits comprising a first oral care composition comprising a bleaching agent, wherein said first oral care composition is adapted to remain on the teeth for at least 30 seconds; a second oral care composition; and instructions for use, are also provided.

22 Claims, No Drawings

(56) References Cited

U.S. PATENT DOCUMENTS

| | | |
|---|---|---|
| 6,576,227 B1 | 6/2003 | Montgomery |
| 6,685,921 B2 | 2/2004 | Lawlor |
| 2002/0006386 A1 | 1/2002 | Ibsen et al. |
| 2003/0211051 A1 | 11/2003 | Majeti et al. |
| 2004/0086468 A1 | 5/2004 | Prosise et al. |
| 2005/0008584 A1 | 1/2005 | Montgomery |
| 2005/0036956 A1 | 2/2005 | Fei et al. |
| 2005/0038181 A1 | 2/2005 | Chopra et al. |
| 2005/0063923 A1 | 3/2005 | Prencipe et al. |
| 2006/0045854 A1 | 3/2006 | Zaidel et al. |
| 2006/0062744 A1 | 3/2006 | Lokken |
| 2006/0147394 A1 | 7/2006 | Shastry et al. |
| 2006/0292091 A1 | 12/2006 | Prosise |
| 2007/0071695 A1 | 3/2007 | Chopra et al. |
| 2007/0253916 A1 | 11/2007 | Maitra et al. |
| 2008/0274066 A1 | 11/2008 | Montgomery |
| 2010/0012891 A1* | 1/2010 | Speronello ............... A61K 8/20 252/186.21 |
| 2010/0028273 A1 | 2/2010 | Fischer et al. |
| 2010/0322988 A1* | 12/2010 | Prencipe ................. A61K 8/22 424/401 |
| 2011/0081628 A1 | 4/2011 | Alden, IV et al. |
| 2012/0282192 A1 | 11/2012 | Miller et al. |
| 2012/0301408 A1* | 11/2012 | Baker .................... A61K 8/736 424/49 |
| 2013/0287710 A1 | 10/2013 | Chopra et al. |
| 2014/0377193 A1 | 12/2014 | Chopra et al. |

FOREIGN PATENT DOCUMENTS

| | | |
|---|---|---|
| EP | 0417971 | 3/1991 |
| EP | 0535816 | 4/1993 |
| GB | 1205325 | 9/1970 |
| RU | 2375040 | 12/2009 |
| WO | WO 91/007184 | 5/1991 |
| WO | WO 00/009079 | 2/2000 |
| WO | WO 02/034221 | 5/2002 |
| WO | WO 03/024415 | 1/2003 |
| WO | WO 03/094877 | 11/2003 |
| WO | WO 05/018591 | 3/2005 |
| WO | WO 05/070378 | 8/2005 |
| WO | WO 05/097053 | 10/2005 |
| WO | WO 06/026424 | 3/2006 |
| WO | WO 06/073822 | 7/2006 |
| WO | WO 07/037961 | 4/2007 |
| WO | WO 07/064885 | 6/2007 |
| WO | WO 12/102750 | 8/2012 |
| WO | WO 14/092732 | 6/2014 |
| WO | WO 14/092733 | 6/2014 |
| WO | WO 14/092736 | 6/2014 |
| WO | WO 14/092737 | 6/2014 |

OTHER PUBLICATIONS

Leonard et al., 1998, "Use of different concentrations of carbamide peroxide for bleaching teeth: an in vitro study," Quintessence Int. 29(8):503-507.

P, 2011, "Is it ok to take some whitening toothpaste and rub it on your front teeth overnight before bed and leave it?" How to Make Your Teeth Whiter http://howtomakeyourteethwhiter.net/q-and-a/is-it-ok-to-take-some-wh . . . te-and-rub-it-on-your-front-teeth-over-night-before-bed-and-leave-it/.

Stookey et al., 1982, "In vitro removal of stain with dentifrices," J. Dental Research 61(11):1236-1239.

Sulieman et al., 2004, "The effect of hydrogen peroxide concentration on the outcome of tooth whitening: an in vitro study," J. Dentistry 32(4):295-299.

Written Opinion in International Application No. PCT/US2012/069835, dated Jan. 19, 2015.

Anonymous, "Whitening teeth with hydrogen peroxide," May 29, 2012, Retrieved from Internet, http://www.mycharm.ru/articles/text?id=4358.

Mendes et al., "Changes in surface roughness and color stability of two composites caused by different bleaching agents," Braz. Dent J., 2012, 23(6): abstract.

* cited by examiner

METHODS FOR WHITENING TEETH

BACKGROUND

Whitening dentifrices are traditionally applied to a toothbrush which is used to administer the product to the teeth. However, there remains a need for more efficient and effective approaches to whitening teeth. Embodiments of the present invention are directed to these ends.

SUMMARY

In some embodiments, the present invention provides a novel regimen designed to maximize the whitening efficacy of a dentifrice. In some embodiments, the regimen comprises two steps and the order in which these steps are performed is not critical to efficacy. In some embodiments, one step of the regimen is to administer a first oral care composition to a tooth using an applicator. In some embodiments, one step of the regimen is to administer a first oral care composition to a tooth using a finger. In some embodiments, the first oral care composition is retained on the tooth for at least 30 seconds. In some embodiments, the first oral care composition is retained on the tooth for between 30 seconds and 120 seconds. Some embodiments of the present invention comprise a second step, wherein a second oral care composition is administered to an oral care implement and the teeth are brushed. In some embodiments, the teeth are brushed for one to three minutes.

In some embodiments, the first oral care composition comprises: a crosslinked polyvinylpyrrolidone complexed with hydrogen peroxide; and an abrasive.

Some embodiments of the present invention provide kits comprising an oral care composition comprising: a first oral care composition comprises a bleaching agent, wherein said first oral care composition is adapted to remain on said tooth for at least 30 seconds; a second oral care composition; and instructions for use. In some embodiments, the instructions for use direct a human subject to administer an effective amount of a first oral care composition comprising a bleaching agent to a tooth, and allow said first oral care composition to remain on said tooth for at least 30 seconds, and brush the teeth with a second oral care composition.

Further areas of applicability of the present invention will become apparent from the detailed description provided hereinafter.

DETAILED DESCRIPTION

The following description of the preferred embodiment(s) is merely exemplary in nature and is in no way intended to limit the invention, its application, or uses.

As used herein, the term "teeth" is meant to include a single tooth as well as a plurality of teeth. Thus, in some instances, the terms "tooth" and "teeth" can be used interchangeably.

As used herein, the phrase "allowing a/the composition to remain on a tooth" means to permit a composition—after it is administered to the surface of a tooth—to reside substantially undisturbed, in the location where it is administered, for a given period of time. By way of example, and not limitation, this is intended to include the administration of a composition to the surface of a tooth, wherein the composition is not brushed off or intentionally manipulated or removed by the user.

As used herein, the phrase "one or both of the oral care compositions" means one or both of the first oral care composition and the second oral care composition.

In some embodiments, the terms "regimen" and "method" are used interchangeably.

In some embodiments, the present invention provides, in a first embodiment, a method (Method 1) of whitening the teeth, comprising the following steps, in any order: (i) administering to the teeth an effective amount of a first oral care composition comprising a bleaching agent (e.g. a peroxide) and allowing the first oral care composition to remain on the teeth for a period greater than 30 seconds, and (ii) brushing the teeth with a second oral care composition. For example, the invention provides 1.1. Method 1 wherein step (i) is performed before step (ii).

1.2. Method 1 or 1.1 wherein one or both of the oral care compositions comprises one or more agents to alleviate dentinal sensitivity, e.g., potassium salts (for example potassium nitrate) and/or arginine.

1.3. Any of the foregoing methods wherein first oral care composition is allowed to remain on the teeth for a period up to 120 seconds; e.g., about 15 to 120 seconds, e.g., about 30 to 120 seconds, e.g., about 30 to 90 seconds, e.g., about 45 to 90 seconds, e.g., about 60 seconds.

1.4. Any of the foregoing methods wherein the bleaching agent is a peroxide source selected from hydrogen peroxide, peroxide salts or complexes, hydrogen peroxide precursors, and combinations thereof, e.g., selected from urea (carbamide) peroxide, polyvinylpyrrolidine-hydrogen peroxide, perborates, percarbonates (e.g. sodium percarbonate), peroxyacids, peroxyphosphates, peroxycarbonates, peroxysilicates, persulphate; for example calcium peroxyphosphate, sodium perborate, sodium carbonate peroxide, sodium peroxyphosphate, and potassium persulfate; and combinations thereof.

1.5. Method 1.3 wherein the peroxide source is hydrogen peroxide, in free form or in the form of a complex with polyvinylpyrrolidone (PVP) or urea.

1.6. Any of the foregoing methods wherein the concentration of the peroxide source is equivalent to 0.1-5% hydrogen peroxide, e.g., equivalent to about 0.5-3% hydrogen peroxide, e.g., equivalent to about 2 to 4% hydrogen peroxide, e.g., equivalent to about 1% hydrogen peroxide, e.g., equivalent to about 2% hydrogen peroxide., e.g., equivalent to about 3% hydrogen peroxide.

1.7. Any for the foregoing methods, wherein the peroxide source is urea peroxide, wherein the urea peroxide is present in one or both of the compositions at a concentration equivalent to about 3% hydrogen peroxide.

1.8. Any for the foregoing methods, wherein the peroxide source is urea peroxide, wherein the urea peroxide is present in one or both of the compositions at a concentration equivalent to about 2.5% hydrogen peroxide.

1.9. Any for the foregoing methods, wherein the peroxide source is sodium percarbonate, wherein the sodium percarbonate is present in one or both of the compositions at a concentration equivalent to about 1% hydrogen peroxide.

1.10. Any of the foregoing methods, wherein the method is performed one to three times daily, e.g., twice daily, for a period of at least three days, e.g., at least seven days, e.g., for a period of 3 to 14 days.

1.11. Any of the foregoing methods wherein the brushing of step two is performed for a period of 30 seconds to three minutes, e.g., optionally about 90 seconds to two minutes.
1.12. Any of the foregoing methods wherein the first oral care composition is a toothpaste.
1.13. Any of the foregoing methods wherein the first oral care composition is a mouthwash.
1.14. Any of the foregoing methods wherein the second oral care composition is a toothpaste.
1.15. Any of the foregoing methods wherein the second oral care composition is a mouthwash.
1.16. Any of the foregoing methods wherein the first oral care composition is administered using an applicator.
1.17. Any of the foregoing methods wherein the first oral care composition is administered by sponging the composition on the teeth.
1.18. Any of the foregoing methods wherein the first oral care composition is administered by painting the composition on the teeth.
1.19. Any of the foregoing methods wherein the first oral care composition is administered by daubing the composition on the teeth.
1.20. Any of the foregoing methods wherein the first oral care composition is administered using a finger.
1.21. Any of the foregoing methods wherein one or both of the oral care compositions comprises one or more polymers selected from polyvinylpyrrolidone, poloxamer, polyethylene glycol, and combinations thereof.
1.22. Any of the foregoing methods wherein one or both of the oral care compositions comprises a fluoride source, e.g., providing a concentration of about 250-5000 ppm, e.g., 500 to 2,500 ppm fluoride ion, e.g., wherein the fluoride ion source is a soluble fluoride salt selected from stannous fluoride, sodium fluoride, potassium fluoride, sodium monofluorophosphate, sodium fluorosilicate, ammonium fluorosilicate, amine fluoride, ammonium fluoride, and combinations thereof, e.g., selected from sodium fluoride and sodium monofluorophosphate.
1.23. Any of the foregoing methods wherein one or both of the oral care compositions comprises a crosslinked polyvinylpyrrolidone complexed with hydrogen peroxide; and an abrasive.
1.24. Any of the foregoing methods wherein one or both of the oral care compositions comprises a calcium abrasive.
1.25. Any of the foregoing methods wherein one or both of the oral care compositions comprises a crosslinked polyvinylpyrrolidone complexed with hydrogen peroxide, and a stabilizing amount of additional linear and/or crosslinked polyvinylpyrrolidone.
1.26. Any of the foregoing methods wherein one or both of the oral care compositions comprises a crosslinked polyvinylpyrrolidone complexed with hydrogen peroxide, and an ethylene oxide, propylene oxide block co-polymer of formula (ethylene oxide)$_x$-(propylene oxide)$_y$, wherein x is an integer of 80-150 and y is an integer of 30-80, having an average molecular weight of greater than 5000 Da.
1.27. Any of the foregoing methods wherein one or both of the oral care compositions comprises (a) a whitening complex comprising crosslinked polyvinylpyrrolidone complexed with hydrogen peroxide, and (b) an ethylene oxide, propylene oxide block co-polymer of average molecular weight greater than 5000 Da, being substantially free of an ethylene oxide, propylene oxide block co-polymer of average molecular weight less than 5000 Da.
1.28. Any of the foregoing methods wherein one or both of the oral care compositions comprises a whitening complex comprising crosslinked polyvinylpyrrolidone complexed with hydrogen peroxide, wherein the whitening complex comprises about 10-30% hydrogen peroxide by weight and about 5-15% total nitrogen by weight.
1.29. Any of the foregoing methods wherein one or both of the oral care compositions comprises a whitening complex comprising crosslinked polyvinylpyrrolidone complexed with hydrogen peroxide, wherein the total amount of the whitening complex is 3-7% by weight of the composition, e.g., about 5.5%, and the total amount of hydrogen peroxide is 0.5-3%, e.g. about 1% by weight of the composition.
1.30. Any of the foregoing methods one or both of the oral care compositions further comprises polyethylene glycol of average molecular weight 400 to 800 Da.
1.31. Any of the foregoing methods wherein one or both of the oral care compositions comprise less than 3% water.
1.32. Any of the foregoing methods wherein one or both of the oral care compositions is a toothpaste comprising a calcium abrasive selected from a calcium phosphate salt and calcium carbonate.
1.33. Any of the foregoing methods wherein one or both of the oral care compositions comprise calcium pyrophosphate.
1.34. Any of the foregoing methods wherein one or both of the oral care compositions comprise comprises the following ingredients by weight:

| | |
|---|---|
| Glycerin | 3-7% |
| Propylene glycol | 20-30% |
| Ethylene oxide, propylene oxide block co-polymer, avg. MW >5 kDa | 5-15% |
| Polyethylene glycol 600 | 5-15% |
| Crosslinked polyvinylpyrrolidone complexed with 15-25% $H_2O_2$ | 3-16.5% |
| Calcium pyrophosphate | 25-45% |

1.35. Any of the foregoing methods wherein one or both of the oral care compositions is a gel non-abrasive composition.
1.36. Any of the foregoing methods wherein one or both of the oral care compositions comprises linear and/or crosslinked polyvinylpyrrolidone, in addition to any crosslinked polyvinylpyrrolidone complexed with hydrogen peroxide, e.g., in an amount of about 9%.
1.37. Any of the foregoing methods wherein one or both of the oral care compositions comprises:

| | |
|---|---|
| Glycerin | 10-55% |
| Propylene glycol | 5-30% |
| Ethylene oxide, propylene oxide block co-polymer, avg. MW >5 kDa | 1-10% |
| Polyethylene glycol 600 | 5-15% |
| Additional linear and/or crosslinked polyvinylpyrrolidone | 1-15% |
| Crosslinked polyvinylpyrrolidone complexed with 15-25% $H_2O_2$ | 3-16.5%. |

1.38. Any of the foregoing methods wherein one or both of the oral care compositions further comprises calcium pyrophosphate at a concentration of from about 0.1 to about 20%, by weight.

1.39. Any of the foregoing methods wherein one or both of the oral care compositions comprises glycerin at a concentration of from about 14 to 32%, by weight.
1.40. Any of the foregoing methods wherein one or both of the oral care compositions comprises propylene glycol at a concentration of from about 9 to about 25%, by weight.
1.41. Any of the foregoing methods wherein one or both of the oral care compositions further comprises 0.01-5%, e.g., sodium acid pyrophosphate, stearic acid coated alumina or a clay (e.g. laponite), e.g., about 0.1%, of an ingredient selected from sodium acid pyrophosphate and stearic acid coated alumina; and/or about 2% of a clay.
1.42. Any of the foregoing methods wherein one or both of the oral care compositions does not exhibit an unacceptable level of phase separation after 60 minutes at 2050 rpm in a LumiSizer 110 analytical centrifuge.
1.43. Any of the foregoing methods wherein one or both of the oral care compositions is substantially the same as Composition A, Composition B, Composition C or Composition D of Example 1 herein.

Some embodiments of the present invention further provide a first oral care composition comprising a peroxide for use in any of the foregoing methods (Method 1, et seq.), and the use of a first oral care composition comprising a peroxide for use in any of the foregoing methods (Method 1, et seq.). In some embodiments, the present invention further provides a kit of parts comprising a first oral care composition comprising fluoride for use in any of the foregoing methods (Method 1, et seq.), together with instructions for use.

In some embodiments, the step performed second is performed within 60 seconds of completion of the step performed first. In some embodiments, the step performed second is performed within 30 seconds of completion of the step performed first. In some embodiments, the step performed second is performed within 15 seconds of completion of the step performed first. In some embodiments, the step performed second is performed immediately after completion of the step performed first.

In some embodiments, step (ii) is performed within 30 seconds of the completion of step (i). In some embodiments, step (ii) is performed within 15 seconds of the completion of step (i).

Some embodiments of the present invention comprise a third step wherein a third oral composition is administered to the oral cavity. In some embodiments, the third oral care composition is a mouthwash. Some embodiments of the present invention comprise a third step wherein a mouthwash is administered to the oral cavity. Some embodiments of the present invention comprise a third step wherein a mouthwash comprising a bleaching agent (e.g., a peroxide source, optionally hydrogen peroxide) is administered to the oral cavity.

The oral care compositions used in the above described methods may in some embodiments, comprise a hydrogen peroxide complex with a polymer, such as polyvinylpyrrolidone. For example, the oral care compositions may comprise a crosslinked polyvinylpyrrolidone complexed with hydrogen peroxide, a stabilizing amount of an additional linear and/or crosslinked polyvinylpyrrolidone, an abrasive and a humectant. Some embodiments utilize oral care compositions comprising: from about 0.5 to about 16.5%, by weight, crosslinked polyvinylpyrrolidone complexed with hydrogen peroxide. Other embodiments utilize oral care compositions comprising: from about 1 to about 15%, by weight, crosslinked polyvinylpyrrolidone complexed with hydrogen peroxide. Still other embodiments utilize oral care compositions comprising: from about 3 to about 12%, by weight, crosslinked polyvinylpyrrolidone complexed with hydrogen peroxide. Yet other embodiments utilize oral care compositions comprising: from about 4 to about 10%, by weight, crosslinked polyvinylpyrrolidone complexed with hydrogen peroxide. While other embodiments utilize oral care compositions comprising: from about 5 to about 8%, by weight, crosslinked polyvinylpyrrolidone complexed with hydrogen peroxide. In some embodiments, the oral care compositions comprise 5.5%, by weight, crosslinked polyvinylpyrrolidone complexed with hydrogen peroxide.

In some embodiments, the present invention utilizes oral care compositions comprising from about 1 to about 20% of an additional linear and/or crosslinked polyvinylpyrrolidone. Some embodiments utilize oral care compositions comprising from about 1 to about 15%, by weight, of an additional linear and/or crosslinked polyvinylpyrrolidone. Some embodiments utilize oral care compositions comprising from about 5 to about 15%, by weight, of an additional linear and/or crosslinked polyvinylpyrrolidone. Other embodiments utilize oral care compositions comprising from about 7 to about 12%, by weight, of an additional linear and/or crosslinked polyvinylpyrrolidone. Further embodiments utilize oral care compositions comprising from about 8 to about 11%, by weight, of an additional linear and/or crosslinked polyvinylpyrrolidone. Still further embodiments utilize oral care compositions comprising from about 8.5 to about 10%, by weight, of an additional linear and/or crosslinked polyvinylpyrrolidone. Still other embodiments utilize oral care compositions comprising 9.5% or 10%, by weight, of an additional linear and/or crosslinked polyvinylpyrrolidone. Yet other embodiments utilize oral care compositions comprising about 9%, by weight, of an additional linear and/or crosslinked polyvinylpyrrolidone.

In some embodiments, one or both of the oral care compositions comprises a peroxide whitening agent comprising a complex of hydrogen peroxide and cross-linked polyvinylpyrrolidone; an abrasive; an anticalculus agent; and a substantially anhydrous carrier; wherein the carrier comprises an ethylene oxide/propylene oxide block copolymer. In some embodiments, one or both of the oral care compositions comprises an abrasive selected from: silica; alumina; calcium pyrophosphate; calcium carbonate; and dicalcium phosphate. In some embodiments, one or both of the oral care compositions comprises an anticalculus agent selected from: a polyphosphate; a hexametaphosphate salt; a polyolefin sulfonate; and a combination of two or more thereof. In some embodiments, the abrasive comprises calcium pyrophosphate. In some embodiments, the abrasive comprises alumina. In some embodiments, the abrasive comprises coated alumina.

In some embodiments, one or both of the oral care compositions comprises a bound peroxide comprising hydrogen peroxide in complex with a cross-linked polyvinyl pyrrolidone; an abrasive having an average particle size of about 1 to about 20 μm; and an orally acceptable substantially anhydrous carrier wherein the carrier comprises a polyethylene glycol/ethylene oxide copolymer or an ethylene oxide/propylene oxide block copolymer.

In some embodiments, one or both of the oral care compositions comprises a whitening agent consisting essentially of hydrogen peroxide complexed with a cross-linked polyvinyl pyrrolidone; an abrasive having an average particle size of about 1 to about 20 μm; and an orally acceptable substantially anhydrous carrier wherein the carrier comprises a polyethylene glycol/ethylene oxide copolymer or an ethylene oxide/propylene oxide block copolymer; wherein the composition is a single-phase toothpaste.

Some embodiments of the present invention utilize gel-based peroxide compositions further comprising a calcium abrasive. In some embodiments, one or both of the oral care compositions comprises from about 9 to about 25%, by weight, propylene glycol. In some embodiments, one or both of the oral care compositions comprises from about 14 to about 32%, by weight, glycerin. In other embodiments, one or both of the oral care compositions comprises less than 20%, by weight, of a calcium abrasive. Some embodiments utilize compositions comprising from about 9 to about 25%, by weight, propylene glycol; from about 14 to about 32%, by weight, glycerin; and less than 20%, by weight, of a calcium abrasive.

Still other embodiments utilize oral care compositions comprising from about 20 to about 60%, by weight, humectant.

Yet further embodiments utilize oral care compositions comprising from about 5 to about 25%, by weight, abrasive.

The oral care compositions of the foregoing methods may have a "low water" content, meaning that a total concentration of water, including any free water and all water contained in any ingredients, is less than about 5%, preferably less than 3%, preferably less than 2% water.

In those embodiments where abrasives are present, the average particle size is generally about 0.1 to about 30 microns, for example about 1 to about 20 or about 5 to about 15 microns.

In some embodiments, the first oral care composition and the second oral care composition are the same.

In some embodiments, the second oral care composition is a non-peroxide composition. In some embodiments, the second oral care composition comprises a bluing agent. In some embodiments, the second oral care composition comprises Pigment Blue 15.

In some embodiments, the second oral care composition comprises silica. In some embodiments, the second oral care composition comprises a fluoride ion source. In some embodiments, the second oral care composition comprises titanium dioxide. In some embodiments, the second oral care composition comprises mica. In some embodiments, the second oral care composition comprises FD&C Blue No. 1. In some embodiments, the second oral care composition comprises sodium laureth 2 phosphate. In some embodiments, the second oral care composition comprises disodium pyrophosphate. In some embodiments, the second oral care composition comprises xylitol. In some embodiments, the second oral care composition comprises fluoride, silica, titanium dioxide, mica, sodium laureth 2 phosphate, FD&C Blue No. 1, xylitol and disodium pyrophosphate.

In some embodiments the first oral care composition is a mouthwash, wherein the mouthwash comprises hydrogen peroxide. In some embodiments the first oral care composition is a mouthwash, wherein the mouthwash comprises hydrogen peroxide and a polyphosphate. In some embodiments the first oral care composition is a mouthwash, wherein the mouthwash comprises hydrogen peroxide and sodium hexametaphosphate. In some embodiments the first oral care composition is a mouthwash, wherein the mouthwash comprises hydrogen peroxide, sodium hexametaphosphate and alcohol. In some embodiments the first oral care composition is a mouthwash, wherein the mouthwash comprises hydrogen peroxide, sodium hexametaphosphate and is alcohol-free. In some embodiments the first oral care composition is a mouthwash, wherein the mouthwash comprises hydrogen peroxide, disodium phosphate and menthol. In some embodiments the first oral care composition is a mouthwash, wherein the mouthwash comprises hydrogen peroxide, disodium phosphate, alcohol and menthol.

In some embodiments the first oral care composition is a mouthwash, wherein the mouthwash comprises hydrogen peroxide, disodium phosphate, alcohol and menthol; and the second oral care composition is a toothpaste comprising urea peroxide at a concentration sufficient to provide about 3% hydrogen peroxide.

In some embodiments, the first oral care composition is a strip comprising a bleaching agent. In some embodiments, the first oral care composition is a dissolvable strip comprising a bleaching agent. In some embodiments, the first oral care composition is a dissolvable strip comprising a bleaching agent, wherein the strip substantially dissolves in about 30 to 90 seconds. In some embodiments, the first oral care composition is a dissolvable strip comprising a bleaching agent; and the second oral care composition is a toothpaste comprising urea peroxide at a concentration sufficient to provide about 3% hydrogen peroxide.

In some embodiments, the first oral care composition comprises a strip comprising a bleaching agent; and the second oral care composition does not contain a bleaching agent. In some embodiments, the first oral care composition comprises a strip comprising a bleaching agent; and the second oral care composition comprises silica, titanium dioxide, mica, sodium laureth 2 phosphate, FD&C Blue No. 1 and disodium pyrophosphate.

In some embodiments, the method provides a $\Delta W^*$ of at least 0.6 after 7 cycles. In some embodiments, the method provides a $\Delta W^*$ of at least 0.75 after 7 cycles. In some embodiments, the method provides a $\Delta W^*$ of at least 1 after 7 cycles. In some embodiments, the method provides a $\Delta W^*$ of at least 1.25 after 7 cycles. In some embodiments, the method provides a $\Delta W^*$ of at least 2 after 7 cycles. In some embodiments, the method provides a $\Delta W^*$ of at least 2.5 after 7 cycles. In some embodiments, the method provides a $\Delta W^*$ of at least 2.75 after 7 cycles.

In various embodiments of the present invention, one or both of the oral care compositions comprises an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. In some embodiments, one or both of the oral care compositions may include a mixture of different anticalculus agents. In some embodiments, tetrasodium pyrophosphate (TSPP) and sodium tripolyphosphate (STPP) are used. In some embodiments, the anticalculus agent comprises TSPP at about 1-2% and STPP at about 7% to about 10%.

The oral care compositions of the above-described methods can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The oral care compositions of the above-described methods may also comprise various ingredients to adjust the rheology and feel of the composition such as humectants, surface active agents, thickening or gelling agents, etc.

The oral care compositions of the above-described methods may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

One or both of the oral care compositions of the above-described methods optionally comprises a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

In various embodiments, the carrier may comprise polymers and/or copolymers of polyethylene glycol, of ethylene oxide/propylene oxide, and of silicone. If such copolymers/polymers are used, they may be selected from commercially available materials. Block copolymers of ethylene oxide/propylene oxide are useful, but higher molecular weight, e.g., >5000 Da are preferred, e.g. including PLURACARE® L1220 (available from BASF, Wyandotte, Mich., United States of America). Low or medium molecular weight polyethylene glycol, e.g., PEG 400, PEG 600, PEG 800, PEG 1000 and mixtures thereof are also useful. It is preferred that the carrier(s) provide a composition with a viscosity of about 10,000 CPS to about 700,000 CPS, preferably about 30,000 CPS to about 300,000 CPS.

As recognized by one of skill in the art, the oral care compositions used in the above described methods may optionally include other materials, such as for example, anti-caries agents (e.g. arginine), desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

In some embodiments, the first oral care composition is substantially free of a salivary stimulant. In some embodiments, the first oral care composition is substantially free of M3 agonists.

In some embodiments, the tooth whitening compositions of the present invention are substantially anhydrous, that is, no water is added. The composition may contain trace levels of water from ingredients or from product manufacture; however, such trace levels are insubstantial and do not interfere with the hydrophobic character of the composition.

In some embodiments, the viscosity of the compositions of the invention is greater than about 1,000 centipoise (cPs) and less than about 900,000 cPs, in a more specific embodiment greater than about 10,000 cP and less than about 100,000 cPs, in a more specific embodiment greater than 50,000 cPs and less than about 900,000 cPs, and in an even more specific embodiment from between about 200,000 cPs to about 600,000 cPs.

In some embodiments, the present invention comprises a hydrophobic component, carrier or base material that comprises a silicone polymer. The term "hydrophobic" or "water-insoluble" as applied to polymers and as employed herein refers to an organic polymer which is substantially non-aqueous having a water solubility of less than one gram per 100 grams of water at 25° C. Any such silicone polymers that are compatible with the whitening agents described herein, and which can produce a tooth whitening composition having a desired viscosity can be used.

In some embodiments, the oral care compositions used in the above described methods comprise an anti-caries effective amount of arginine.

Flavorants, sweeteners, colorants, foam modulators, mouth-feel agents and others additively may be included if desired, in the compositions described herein.

The oral care compositions used in the above described methods may optionally include one or more further active material(s), which is operable for the prevention or treatment of a condition or disorder of hard or soft tissue of the oral cavity, the prevention or treatment of a physiological disorder or condition, or to provide a cosmetic benefit.

The oral care compositions used in the above described methods may optionally include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The oral care compositions used in the above described methods may optionally include an antimicrobial (e.g., antibacterial) agent. An illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%.

The oral care compositions used in the above described methods may optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The oral care compositions used in the above described methods may optionally comprise an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

The above described methods, e.g., Method 1, et seq., may be administered as required for whitening, and the frequency and duration of use of the methods will vary based on individual needs. In some embodiments, the method is carried out regularly, e.g., on a daily basis, at least one time daily for multiple consecutive days, or alternately every second or third day or once or twice weekly. The method may be carried out regularly over a period of days or weeks, for example for two, three, four, or five days, or up to a week, or up to two weeks, and the administration may be intermittent, e.g., every other day or every other week, or one week a month.

Some embodiments of the present invention provide kits comprising an oral care composition comprising: a first oral care composition comprises a bleaching agent, wherein said first oral care composition is adapted to remain on said tooth for at least 30 seconds; a second oral care composition; and instructions for use. In some embodiments, the instructions for use direct a human subject to administer an effective amount of a first oral care composition comprising a bleaching agent to a tooth, and allow said first oral care composition to remain on said tooth for at least 30 seconds, and brush the teeth with a second oral care composition.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Compositions comprising 1% hydrogen peroxide in the form of 5.5% cross-linked polyvinylpyrrolidone-hydrogen peroxide complex (cPVP-$H_2O_2$ complex), for use in the methods of the invention, are prepared using the following ingredients:

Composition A

| Ingredient | Weight % |
| --- | --- |
| Phosphoric Acid | 0.2 |
| Pluracare L1220F | 10 |
| Glycerin | 5 |
| Polyethylene Glycol 600 | 10 |
| Propylene Glycol | 24.62 |
| cPVP-$H_2O_2$ complex (~1% $H_2O_2$) | 5.5 |
| Tetrasodium Pyrophosphate | 2 |
| Sucralose | 0.05 |
| Sodium Saccharin | 0.6 |
| Sodium Mono fluorophosphate | 1.14 |
| Calcium Pyrophosphate | 35.11 |
| Fumed silica | 1.5 |
| Butylated Hydroxytoluene | 0.03 |
| Flavor | 2.25 |
| Sodium Lauryl Sulfate | 2 |
| Total | 100 |

Composition B

| Ingredient | Weight % |
| --- | --- |
| Phosphoric Acid | 0.2 |
| Pluracare L1220F | 10 |
| Glycerin | 5 |
| Polyethylene Glycol 600 | 10 |
| Propylene Glycol | 24.9 |
| cPVP-$H_2O_2$ complex (~1% $H_2O_2$) | 5.5 |
| Tetrasodium Pyrophosphate | 2 |
| Sucralose | 0.05 |
| Sodium Saccharin | 0.6 |
| Sodium Monofluorophosphate | 0.76 |
| Calcium Pyrophosphate | 35.11 |
| Fumed silica | 1.5 |
| Butylated Hydroxytoluene | 0.03 |
| Flavor | 2.25 |
| Sodium Lauryl Sulfate | 2 |
| Sodium Acid Pyrophosphate | 0.1 |
| Total | 100 |

Composition C

| Ingredient | Weight % |
| --- | --- |
| Phosphoric Acid | 0.2 |
| Pluracare L1220F | 10 |
| Glycerin | 5 |
| Polyethylene Glycol 600 | 10 |
| Propylene Glycol | 24.9 |
| cPVP-$H_2O_2$ complex (~1% $H_2O_2$) | 5.5 |
| Tetrasodium Pyrophosphate | 2 |
| Sucralose | 0.05 |
| Sodium Saccharin | 0.6 |
| Sodium Monofluorophosphate | 0.76 |
| Calcium Pyrophosphate | 35.11 |
| Fumed silica | 1.5 |
| Butylated Hydroxytoluene | 0.03 |
| Flavor | 2.25 |
| Sodium Lauryl Sulfate | 2 |
| Coated Alumina | 0.1 |
| Total | 100 |

Composition D

| Ingredient | Weight % |
| --- | --- |
| Phosphoric Acid | 0.2 |
| Pluracare L1220F | 10 |
| Glycerin | 5 |
| Polyethylene Glycol 600 | 10 |
| Propylene Glycol | 25 |
| cPVP-$H_2O_2$ complex (~1% $H_2O_2$) | 5.5 |
| Tetrasodium Pyrophosphate | 2 |
| Sucralose | 0.05 |
| Sodium Saccharin | 0.6 |
| Sodium Mono fluorophosphate | 0.76 |
| Calcium Pyrophosphate | 35.11 |
| Fumed silica | 1.5 |
| Butylated Hydroxytoluene | 0.03 |
| Flavor | 2.25 |
| Sodium Lauryl Sulfate | 2 |
| Total | 100 |

Example 2

In-vitro testing is conducted in order to compare the efficacy of regimens according to the claimed invention and a traditional brushing regimen. This testing is carried out using first and second oral care compositions containing 1% hydrogen peroxide (5.5% cross-linked polyvinylpyrrolidone-hydrogen peroxide complex), in accordance with Composition D of Example 1.

Three different regimens—as described in Table 1 (below)—are evaluated.

TABLE 1

| Regimen | Direct Administration Residence Time (seconds) | Brushing Time (seconds) | Total Exposure Time (seconds) |
| --- | --- | --- | --- |
| 1 | 0 | 120 | 120 |
| 2 | 45 | 75 | 120 |
| 3 | 90 | 30 | 120 |

The following procedure is used for each regimen with the time of each step being the only variable. Four human tooth sections are mounted in a tray using a thermally setting impression compound and a total of two trays are tested with each regimen, for a total of eight tested with each regimen. To minimize variations between human samples, one section from each tooth is treated with each regimen. Once the teeth are mounted in the tray, baseline color measurements are made using a spectrophotometer. L*, a*, and b* values are measured and used to calculate the baseline whiteness index, W*, for each section. After baseline color measurements the teeth are hydrated by soaking in water. To begin the brushing study, 12.5 g of a composition containing an ingredient to bleach stains (in this example 1% hydrogen peroxide) is weighed directly into the tray with the requirement that each tooth was covered by a composition. The composition is allowed to directly contact the teeth for the time specified in the table above. Next, 12.5 g of artificial saliva is added to the tray and the teeth are brushed at 120 strokes/min, with 250 g of pressure, for the time indicated in the table. Following 120 seconds of treatment with each regimen, the teeth are rinsed with 100 mL of deionized water, blotted dry, and color measurements made with a spectrophotometer. This process is repeated for a total of seven cycles. The change in whiteness index after seven brushing cycles as compared to baseline is calculated for each regimen. ($\Delta W^* = W^*_{treated} - W^*_{baseline}$).

One-way analysis of variance is used to compare the mean $\Delta W^*$ results for the three regimen groups. A Tukey multiple comparison test is used to assess pair-wise differences among the regimen groups. The results are summarized in Table 2 (below).

TABLE 2

| Regimen | N | Mean $\Delta W^*$ | St Dev | P value | Tukey Groups |
| --- | --- | --- | --- | --- | --- |
| 1 | 8 | −0.52 | 0.4 | 0.004 | A |
| 2 | 8 | −1.32 | 1.5 | | A B |
| 3 | 8 | −2.82 | 1.4 | | B |

The ANOVA analysis indicates highly significant differences among the regimen groups (p=0.004). Subsequent Tukey analysis indicated that the 0 and 90 second regimen groups are significantly different from each other.

The results described in Table 2 (above) demonstrate that an exemplary regimen of the claimed invention, wherein a composition comprising a bleaching agent is administered to the teeth and allowed to remain on the teeth for a period of time; and wherein the teeth are brushed with a composition, provides a significant increase in whitening efficacy versus brushing alone even when the total exposure time to the bleaching agent is held constant.

We claim:

1. A regimen for whitening teeth, comprising the following steps:
   (i) administering an effective whitening amount of an oral care composition comprising a bleaching agent to a tooth, and
   (ii) allowing said oral care composition to remain on said tooth for a period of 45 to 90 seconds, and
   (iii) brushing the tooth with the oral care composition,
   wherein said bleaching agent is present in an amount equivalent to 0.1-5% hydrogen peroxide,
   wherein step (i) is performed before step (ii), and
   wherein said bleaching agent is crosslinked polyvinylpyrrolidone complexed with hydrogen peroxide in an amount of 1 to 15% by weight of the composition.

2. The regimen of claim 1, wherein the total exposure time of the tooth to the oral care composition is about 120 seconds.

3. The regimen of claim 1, wherein step (ii) is performed within 30 seconds of the completion of step (i).

4. The regimen of claim 1, wherein step (ii) is performed within 15 seconds of the completion of step (i).

5. The regimen of claim 1, wherein said oral care composition comprises an agent to alleviate dentinal sensitivity.

6. The regimen of claim 1 wherein the concentration of said bleaching agent is equivalent to about 1% hydrogen peroxide.

7. The regimen of claim 1 wherein the concentration of said bleaching agent is equivalent to from about 2 to about 4% hydrogen peroxide.

8. The regimen of claim 1, wherein said bleaching agent is equivalent to about 3% hydrogen peroxide.

9. The regimen of claim 1, wherein said regimen is performed one to three times daily, for a period of 3 to 14 days.

10. The regimen of claim 1, wherein said oral care composition is administered using an applicator.

11. The regimen of claim 1, wherein said oral care composition is administered using a finger.

12. The regimen of claim 1 wherein said oral care composition comprises a fluoride source.

13. The regimen of claim 1 wherein said oral care composition further comprises an ethylene oxide, propylene oxide block co-polymer of formula (ethylene oxide)$_x$-(propylene oxide)$_y$ wherein x is an integer of 80-150 and y is an integer of 30-80, having an average molecular weight of greater than 5000 Da.

14. The regimen of claim 13 wherein said ethylene oxide, propylene oxide block co-polymer of average molecular weight greater than 5000 Da, is substantially free of an ethylene oxide, propylene oxide block co-polymer of average molecular weight less than 5000 Da.

15. The regimen of claim 13 wherein said oral care composition further comprises polyethylene glycol of average molecular weight 400 to 800 Da.

16. The regimen of claim 13, wherein said oral care composition further comprises an abrasive.

17. The regimen of claim 16 wherein said oral care composition comprises calcium pyrophosphate.

18. The regimen of claim 13 wherein said oral care composition further comprises 0.01-1% of an ingredient selected from sodium acid pyrophosphate and stearic acid coated alumina.

19. The regimen of claim 13 wherein said oral care composition further comprises a bluing agent.

20. The regimen of claim 16, wherein said oral care composition further comprises a bluing agent.

21. A kit comprising:
an oral care composition comprising a bleaching agent, wherein said oral care composition is adapted to remain on said tooth for a period of 45 to 90 seconds; and
instructions for use,
wherein the concentration of said bleaching agent is equivalent to 0.1-5% hydrogen peroxide, and
wherein said bleaching agent is crosslinked polyvinylpyrrolidone complexed with hydrogen peroxide in an amount of 1 to 15% by weight of the composition.

22. The kit of claim 21, wherein the instructions for use direct a human subject to administer an effective amount of an oral care composition comprising a bleaching agent to a tooth, and allow said oral care composition to remain on said tooth for a period of 45 to 90 seconds, and brush the tooth with the oral care composition.

* * * * *